(12) United States Patent
Groholy

(10) Patent No.: US 11,167,056 B1
(45) Date of Patent: Nov. 9, 2021

(54) AIR DISINFECTION DEVICE USING OZONE FOR KILLING VIRUSES, FUNGI AND BACTERIA, AS WELL AS AN OZONE RECOMBINATION UNIT

(71) Applicant: Tibor Gabor Groholy, Budapest (HU)

(72) Inventor: Tibor Gabor Groholy, Budapest (HU)

(73) Assignee: Istvan Hirosik, Ontario (CA)

( * ) Notice: Subject to any disclaimer, the term of this patent is extended or adjusted under 35 U.S.C. 154(b) by 0 days.

(21) Appl. No.: 17/192,497

(22) Filed: Mar. 4, 2021

(30) Foreign Application Priority Data

Feb. 8, 2021 (CA) .............................. CA 3108550

(51) Int. Cl.
*A61L 9/04* (2006.01)
*A61L 9/12* (2006.01)
*A61L 9/20* (2006.01)
*C01B 13/11* (2006.01)
*A61L 101/02* (2006.01)

(52) U.S. Cl.
CPC .............. *A61L 9/046* (2013.01); *A61L 9/122* (2013.01); *A61L 9/20* (2013.01); *C01B 13/115* (2013.01); *A61L 2101/02* (2020.08); *A61L 2209/12* (2013.01); *A61L 2209/212* (2013.01); *C01B 2201/14* (2013.01); *C01B 2201/40* (2013.01); *C01B 2201/82* (2013.01)

(58) Field of Classification Search
CPC . A61L 9/046; A61L 9/122; A61L 9/20; A61L 2209/12; A61L 2209/212; A61L 2101/02; C01B 13/115; C01B 2201/40; C01B 2201/82; C01B 2201/14
See application file for complete search history.

(56) References Cited

U.S. PATENT DOCUMENTS

| 4,574,326 A | * | 3/1986 | Myochin | ................. H01T 19/00 |
| | | | | 250/324 |
| 8,557,188 B2 | | 10/2013 | Lo | |
| 2005/0158219 A1 | * | 7/2005 | Taylor | .................... B01D 53/32 |
| | | | | 422/121 |
| 2012/0141322 A1 | | 6/2012 | Fogg | |

FOREIGN PATENT DOCUMENTS

| EP | 1973578 B1 | 4/2013 |
| WO | 9734682 A1 | 9/1997 |

* cited by examiner

*Primary Examiner* — Sean E Conley
*Assistant Examiner* — Brendan A Hensel
(74) *Attorney, Agent, or Firm* — Laurence A. Greenberg; Werner H. Stemer; Ralph E. Locher

(57) ABSTRACT

Air disinfection device using ozone for killing bacteria and viruses with ozone recombination unit, comprising a housing (10), a fan (20), an ozone generator (50) included in the housing (10) and arranged in a separate box (30), the ozone generator (50) is electrically driven by a supply unit (41) connecting a high voltage to the ozone generator (50) to excite corona discharge, wherein a germicidal lamp (40) light is arranged in the box (30), and both the germicidal lamp (40) and the ozone generator (50) are driven by electric pulses having a frequency over 10 KHz, and an ozone recombination unit (60) is arranged behind the box (30) across the airflow passage to neutralize ozone included in the air flow that comprises at least two windings (63, 64) each having at least one surface comprised of respective spaced wires positioned across the airflow path and connected to a supply unit (61) coupling a pulsated high voltage with a repetition frequency over 10 kHz between the windings (63, 64).

13 Claims, 2 Drawing Sheets

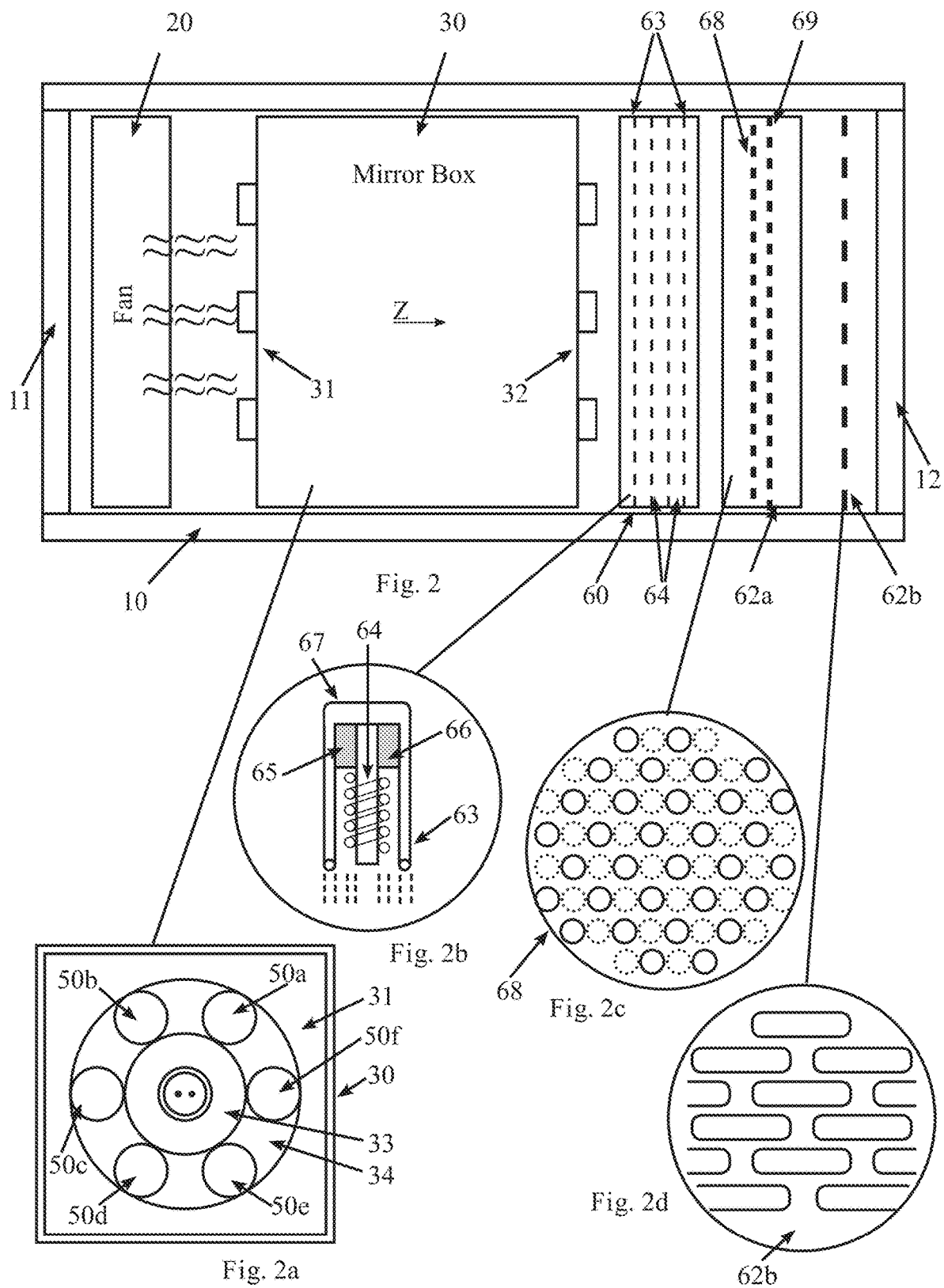

AIR DISINFECTION DEVICE USING OZONE FOR KILLING VIRUSES, FUNGI AND BACTERIA, AS WELL AS AN OZONE RECOMBINATION UNIT

This application claims the benefit of priority from Canadian Patent Application Serial No. 3,108,550, filed Feb. 8, 2021, which is hereby incorporated herein by reference.

The invention relates to an air disinfection device using ozone for viruses, fungi and bacteria provided with an ozone recombination unit, comprising a housing, a fan arranged in the housing for forcing air to pass through the housing, an ozone generator included in the housing and arranged in a separate box which is positioned across the path of the airflow, and the ozone generator is electrically driven by a supply unit connecting a high voltage to said ozone generator to excite corona discharge.

The removal of bacteria and viruses from air is a long known task and there are different ways for solving this task. One of the most efficient ways include the use of ozone which has a high sterilizing potential, but if sufficient amount of ozone is used for this purpose, the room to be sterilized in this way should be emptied and after the sterilization a thorough ventilation is required in the room and no one can enter for more than at least 30 minutes.

Such a device is published in EP 1 973 578 B1 wherein it is described when the device is used, the room is evacuated of personnel. In the device in addition to ozone UV light is used, and one can read there that "the UV light and ozone work alone and synergistically to destroy pathogens. Particularly, the ozone is able to reach non-reflected surfaces because of its gaseous nature."

The different types of air sterilizers are summarized in the description of the prior art portion of the publication US 2012/014 1322A1 mentioning a common problem of UV irradiation-based sterilizers according to which "none of the above-identified apparatuses appear to be configured to effectively monitor and maintain the UV source of the apparatus at substantially maximum output levels." This statement indicates that the UV sources must operate under maximum output level.

The limited lifetime of components of UV photocatalytic air purifier/sterilizer systems is mentioned as a problem is included in U.S. Pat. No. 8,557,188 B2. It lists limited-lifetime components (such as the UV light, UV light electronics, and catalytic portion) and suggests the packaging of such components together to form a single, hand held, unitized package, designed for easy insertion and removal into an air purifier. This is an escape solution of the problem because what is really needed is the use of a system in which the components have long lifetime and no replacement is required.

Finally, reference is made to the publication WO 97/034682 A1 in which ozone is used for sterilization but for attaining the required effect, a long meandering airflow path was provided so that the air to be sterilized is exposed to ozone for a longer time. In the publication UV irradiation was used in addition to the exposure of the airflow to ozone. Because ozone cannot be left to escape from the apparatus when used in a room, the publication uses a catalytic converter in which charcoal or molybdenum disulfide catalysts recombine ozone to $O_2$. The drawback of such a system lies in that catalytic converters will soon get saturated during excess use, and require frequent replacement which is expensive and inconvenient, and when they are close to saturation ozone can enter the airspace of the room which is dangerous to the health of the persons in that space.

Especially in the recent period when the worldwide presence of COVID 19 virus causes high problems to the mankind the efficient and reliable removal of viruses, bacteria and germs from closed air spaces where people stay, mainly in hospital rooms, airplanes, cinemas, theaters, offices and normal living rooms is an acute task. The air disinfection should be solved with maximum efficiency, with high reliability of the operation that does not require frequent maintenance and replacement of any component, that prevents the entering of ozone or unwanted irradiation into the protected airspace and finally which operates with small energy consumption.

The main objective of the invention is to provide a device that can satisfy all of the listed requirements. Within this objective a second objective lies in providing an ozone recombination device that does not require any filter material that should be replaced time to time or any chemical entity for neutralizing ozone.

The solution of the main objective is based on a number of recognitions which can be summarized as follows. Previously the two known disinfection methods, namely UV-C irradiation and using ozone were used with the purpose of providing maximum power of UV-C light and maximum concentration of ozone instead of providing maximum sterilization efficiency. It has been realized that the simultaneous exposure of a pulsated UV-C light with a frequency higher than about 10 KHz and a pulsated generation of corona discharges in an ozone generator to an airflow can provide a maximum sterilization effect with minimum energy consumption.

A further discovery lies in that the recombination of ozone can be provided by using a pulsated high electric field across the passage of airflow, wherein the frequency of the pulses is higher than about 10 KHz and the field strength is slightly under the threshold where corona discharge takes place. Such an ozone recombination device does no use any catalyst or material that would need replacement, has minimum energy consumption and is capable of removing ozone from the air stream, thus the ozone-based sterilization can be used in closed spaces with the presence of people.

For solving the above objectives and utilizing these recognitions an air disinfection device has been provided using ozone for killing bacteria and viruses together with an ozone recombination unit, that comprises a housing, a fan arranged in the housing for forcing air to pass through the housing, an ozone generator included in the housing and arranged in a separate box which is positioned across the path of the airflow, the ozone generator is electrically driven by a supply unit connecting a high voltage to the ozone generator to excite corona discharge, and according to the invention a germicidal lamp emitting UV-C light is also arranged in the box, both the germicidal lamp and the ozone generator are driven by electric pulses having a frequency over 10 KHz, and an ozone recombination unit is arranged behind the box across the airflow passage to neutralize ozone included in the air flow that comprises at least two windings each having at least one surface comprised of respective spaced wires positioned across the airflow path and connected to a supply unit coupling a pulsated high voltage with a repetition frequency over 10 KHz between the windings, wherein the voltage is smaller than required for generating a corona discharge but sufficiently high to force ozone to get recombined into oxygen.

In a preferred embodiment the ozone generator comprises a tube of an electrically insulating material and respective windings are arranged around the outside of the tube and within the interior of the tube, wherein the outer winding substantially covers the inner winding so that the distance between them is constituted by the thickness of the tube.

It is preferred if the germicidal lamp is arranged centrally in the box and a predetermined number of identically designed ozone generators are arranged around the lamp in an even angular distribution, wherein the windings of all of the ozone generators are connected in parallel. The number of the ozone generators is preferably six.

For intensifying the effect of UV irradiation the interior surface of the box is at least partly light reflective.

According to a preferred embodiment the width, frequency and amplitude of the pulses coupled to the germicidal lamp, to the ozone generators and to the ozone recombining unit can be controlled within a predetermined range.

The mechanical structure will be simpler if the box has a planar front plate and a planar rear plate and both of them comprise a central circular piece in which an end portion of the lamp is held, and a ring like opening is formed around the circular piece in which ends of the tubes of the ozone generators are fixed.

It is preferred if the ozone generators are driven by a voltage around 40 KV and a frequency around 40 KHz and the windings of the ozone recombination unit are driven by pulses around 40 KV and frequency around 16 KHz.

It is furthermore preferred if the germicidal lamp is driven by pulses with an intensity of around 100 V and frequency of around 16 KHz.

For further increasing ozone recombination spaced plates of non transparent material can be arranged past the ozone recombining unit wherein the plates are provided with non overlapping holes to make air particles to abut at least one of the plate surfaces during their path.

It s preferred if an UV light screening perforated plate is arranged before the outflow end of the box. o get out of the housing after the ozone recombining unit an UV filter is arranged provided with holes for allowing passage of said airflow.

It is further preferred if in the ozone recombination unit the windings are wound on respective first and second frames, wherein the windings comprise linear spaced wires and the wires are wound to have respective wired planes both at the front and the rear surface of the associated frame, and the second winding is an inner winding wound on the second or inner frame and being arranged within the first or outer frame of the first or outer winding, and the wires of the first and second windings extend normal to each other.

It is preferred if the fan has an adjustable speed and a separate supply unit is connected to it that supplies it with modulated pulses having an adjustable frequency to adjust the speed between 300 rpm and 1500 rpm.

According to the invention an ozone recombination unit has also been provided to be placed across the flow of ozone containing air for neutralizing ozone included in the air flow and the unit comprises at least two windings each having at least one surface comprised of respective spaced wires positioned across the airflow path and connected to a supply unit coupling a pulsated high voltage with a repetition frequency over 10 KHz between the windings, wherein the voltage is smaller than required for generating a corona discharge but sufficiently high to force ozone to get recombined into oxygen.

In the unit it is preferred if the windings are wound on respective first and second frames, wherein the windings comprise linear spaced wires and the wires are wound to have respective wired planes both at the front and the rear surface of the associated frame, and the second winding is an inner winding wound on the second or inner frame and being arranged within the first or outer frame of the first or outer winding, and the wires of the first and second windings extend normal to each other.

The invention has perfectly solved the tasks set, and the simultaneous pulsated supply of UV light and ozone has an increased effect on bacteria and viruses present in the box and either kill them or make them unable to multiply.

The invention will now be described in connection with preferred embodiments thereof in which reference will be made to the accompanying drawings. In the drawing:

FIG. 2 shows a schematic sectional elevation view of the device;

FIG. 2a shows an enlarged front view of the mirror box;

FIG. 2b shows an enlarged detail of the recombination unit;

FIG. 2c shows a detail of the additional ozone filter; and

FIG. 2d shows a detail of an additional UV filter.

Figure 1:
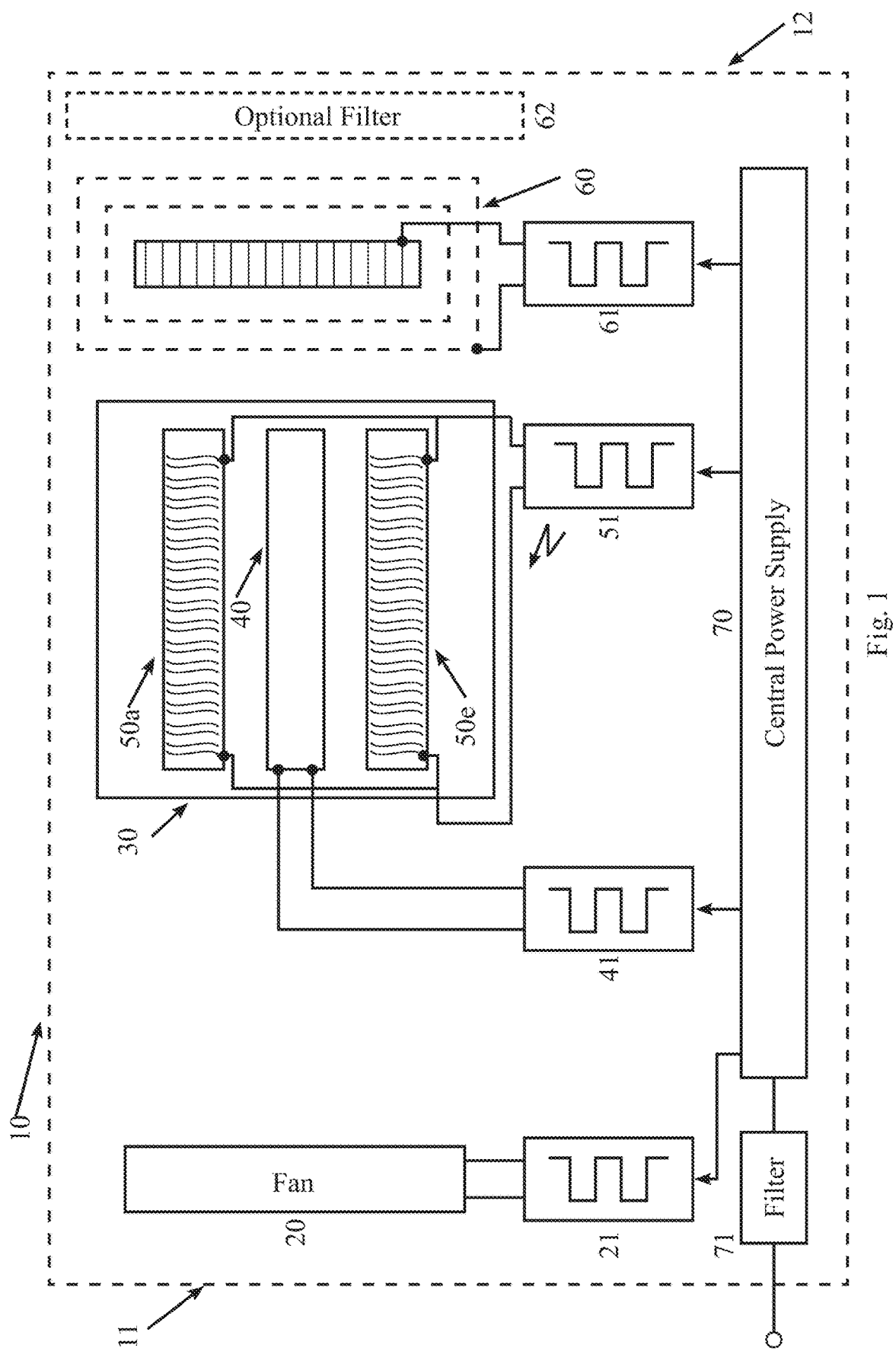
FIG. 1 shows the simplified schematic block diagram of a preferred embodiment of the device.

Reference is made now to FIG. 1 that shows the functional block diagram of the subject virus and bacteria killing device, that comprises a metal, preferably steel housing 10 in which all functional units are arranged and which also provides an electromagnetic shield around the functional units to prevent the environment from spurious electromagnetic noise. The housing 10 has a front plate 11 and a rear plate 12, and both are provided with a plurality of holes for providing passage for air to flow in and out from the housing 10.

Directly behind the front plate 11 a fan 20 is arranged which is the type that is driven by pulse width modulated (PWM) pulses, and its speed can be controlled by the frequency and on/off ratio of the pulses within a wide range. The mean frequency is around 25 kHz and the pulse voltage is 12 V. A separate first controlled PWM supply unit 21 is coupled to the fan 20 by which the airflow rate can be adjusted. The air is forced to flow between the front and rear walls 11, 12 of the housing 10 which is referred to as length direction or direction Z as shown in FIG. 2. The air flows substantially in a laminar stream. A special mirror box 30 is arranged in front of the fan 20 in which two separate functional units are arranged in an integrated way, namely an elongated UV lamp 40 extending centrally along the length of the mirror box 30 and six ozone generators 50a, 50b, 50c, 50d, 50e and 50f which are formed by respective tubes and they are arranged in equal angular spacing around the UV lamp 40 (see FIG. 2a). In the exemplary embodiment the six ozone generators have the same design and also extend in the direction Z trough the mirror box 30.

The UV lamp 40 is a germicidal lamp of the UV-C type that emits UV light in and around the 254 nm range of wavelengths, and it is supplied also with PWM pulses of a second supply unit 41, wherein the frequency and the duty cycle of the pulses can be adjusted. The frequency is around 16 KHz and the peak voltage is around 100 V.

The mirror box 30 has a front plate 31 and a similarly designed rear plate 32 that fit in the square interior thereof as shown in FIG. 2a. In the exemplary embodiment a central circular piece 33 is provided as inner part of the front plate 31 (and a similar one provided in the rear plate 32) that has a central opening which fits to the outer diameter of the UV lamp 40 and holds the same. The UV lamp 40 extends centrally along the longitudinal axis of the mirror box 30 and the respective ends extend out from the front and rear plates 31, 32, whereby there is place for the connection of its electrical contacts. A preferred diameter of the UV lamp 40 is 20 mm.

Both the front and rear plates 31, 32 of the mirror box 30 have respective ring-shaped openings 34 around the central circular piece 33 which has radial size equal with the diameter of tubes of the ozone generators 52a, 52b, 52c, 52d, 52e and 52f which are positioned and held in even angular distribution in the ring-shaped opening 34. The body of the respective ozone generators is formed by the tubes fixed at their both ends to the front and rear plates 31, 32 at their outer portions. The tubes of the ozone generators 52a to 52f are made preferably of special quartz glass transparent for UV-C light, and the mechanical connection can be provided by any known ways, wherein a preferred way is the use of an appropriate adhesive. The diameter of the tubes is preferably around 20 mm. The ring-like opening 34 allows air driven by the fan 20 into the interior of the mirror box 30 in such a way that air flows between the tubes of the ozone generators 52a to 52f and through the inner passages within the respective tubes 52a to 52f and leave the interior over the similar ring like opening in the rear plate 32.

Around the outer surface of each tube that forms the respective ozone generators 52a to 52f a helically arranged outer spiral winding is provided, and in a similar way in the interior surface of each tube a helically wound inner spiral winding is made. The outer and inner windings have the same pitch and arranged so to cover each other, i.e. between them only the wall thickness of the quartz tube defines the distance. In a preferred embodiment this distance is around 1.5 mm. There are several ways of arranging the windings which should resist the presence of ozone and the intensive UV-C light, and the best choice for the material of these windings can be a wire made of non-corrodible steel or a steel alloy. If the inner winding is wound to have a diameter slightly greater than the inner hole of the quartz tube, then by the squeezing of this winding it can be inserted in the tube and then the resilience of the winding will try to expand and press it to the inner wall which stabilizes the position. There are several ways of placing the outer winding on the outside of the tube that can be a similar press-connection but the use of an adhesive can also be a solution. The ends of the respective inner and outer windings constitute the lead out terminals of the respective ozone generators 50a to 50f, and they are connected in parallel and coupled to a further supply unit 51.

It has been explained that the six ozone generators 50a to 50f surround the centrally extending UV-C lamp 40 and this arrangement fills the whole interior of the mirror box 30. The inner surfaces of the plates or covers constituting the mirror box 40 are preferably covered by a light reflecting layer and act as mirrors, whereby the UV-C light radiation emitted by the lamp 40 will have numerous reflections and the light rays will illuminate the whole interior of the mirror box 30. The quartz glass surfaces of the six tubes 52a to 52f also reflect the incident light therefore the UV-C light will reach all parts of the interior of the mirror box 30.

The third PWM supply unit 51 generates high voltage pulses with an adjustable frequency around 40 KHz and the peak voltage is around 40 KV. The parameters of this pulsated voltage are chosen in such a way that a corona discharge is formed between the outer and inner windings of each ozone generator 50a to 50f, whereby the generated ozone will fill the interior of the mirror box 30.

Behind the mirror box 20 an ozone recombination unit 60 is arranged which has the task of forcing the $O_3$ molecules present in the inflowing air to get recombined so that normal ozone-free air should leave the unit 60 and the housing 10. This ozone recombination unit 60 is supplied by a fourth PWM power supply 61 which generates pulses around 16 KHz and the pulse voltage is also around 40 kV.

The four different PWM supply units 21, 41, 51 and 61 are fed from a central power supply 70 which is a step down type converter that generates converted DSC output voltage of around 11V from a DC input supply of around 12V. The task of this power supply 70 is to prevent the passage of unwanted spurious signals outside the device and has an efficient spurious signal rejection property in a wide frequency range. A standard mains filter 71 provides further screening of unwanted signals.

Behind the ozone recombination unit 60 optional filters 62 can be arranged that further enhance the recombination of ozone and can also prevent the passage of unwanted UV light out of the housing 10.

FIG. 2 shows substantially the same arrangement as in FIG. 1 however now the electronic units were not shown and the size of the different units in the drawing correspond more to the actual size of these units as positioned in the housing 10. In fact, FIG. 2 is an elevation sectional view of the device. The fan 20 generates a forced airflow in the longitudinal direction Z in the interior of the housing 10, because both the front and rear plates 11, 12 are perforated and a plurality of openings allow the passage of air therethrough. The speed of the fan 20 can be adjusted between about 300 rpm and 1500 rpm (revolutions per minute) and the most frequently used range is between about 800 and 1200 rpm, whereby the flow rate varies between about 20-25 $m^3$/h. The inflowing air might contain bacteria and viruses which should be killed or made inactive within the mirror box 30, and the air leaving the mirror box 30 is free of any living or active bacteria or virus.

The ozone recombination unit 60 comprises two nets formed of vertical and horizontal wires wound and arranged in different spaced planes. FIG. 2 has a distorted illustration in the sense that two separate windings i.e. outer winding 63 and inner winding 64 are wound on respective rectangular spaced frames 65, 66. There is a space between each adjacent wire in the windings so that air can flow through the windings. The plane of the windings is normal to the flow direction Z, and also normal to each other.

In FIG. 2b there is an enlarged detail of the ozone recombining unit 60, parts of the two spaced frames 65, 66 can be seen, which are made of a planar non-conductive material with rectangular shapes and have a large open interior. The spacing is around 3 mm. The inner winding 64 is wound around the two frames in a horizontal direction and the cross section of the respective wires in FIG. 2b looks like little circles. At the outer part of the frames 65, 65 respective distance members are provided, and the outer winding 63 is wound in vertical direction around the outer part of the distance members, and in FIG. 2b a wire 67 of a part of a vertical loop (or turn) of the outer winding 63 is illustrated (in a distorted view). In this way in the airflow direction Z the air flows first through the front plane defined by the outer wires (that extend in vertical direction) of the outer winding 63, then crosses the horizontal front wires of the inner winding 64, wherein the spacing here is around 2.5 to 3 mm, then proceeds through the spacing between the two frames 65, 66 which is around 3 mm, and flows through the rear horizontal wires of the inner winding 64 and finally flows through the rear vertical wires of the outer winding 63 and proceeds towards the rear plate 12.

In this way the air proceeds twice between the air gaps formed between the outer and inner windings 63, 64 and it is exposed to the effect of the electromagnetic fields established between the two windings 63, 64 by the pulses of the fourth supply unit 61.

The electric field has opposite direction between the first two winding planes and the third and fourth winding planes at each moment. Because the wires of the oppositely located wires are extending normal to each other, the field strength will have a different shape compared to the field which prevailed in the ozone generators, wherein the wires with opposite polarity are extending parallel to each other. In contrast thereto the wires in the windings of the recombination unit 60 extend normal to each other and they are closest to each other at the virtual crossing points only. When the amplitude of the pulses switched between the two windings 63, 64 is below the value at which corona discharge take place, this specific filed will cause ozone molecules to recombine to oxygen.

Behind the ozone recombining unit 60 two different kinds of optional filters 62a and 62b can be arranged. The first comprises a pair of spaced metal plates 68, 69 extending normal to the airflow direction, and each of them has a high number of circular openings shown in the enlarged picture of FIG. 2c where the openings of the first plate 68 are drawn by full line and the ones in the second plate 69 are drawn by dotted lines. These openings have a diameter of around 3 to 4 mm and the openings in the two plates 68, 69 are offset relative to each other when seen from the flow direction Z, so that air cannot flow through the pair of the plates 68, 69 because their path will be broken and they have to have sudden changes in their flow direction by abutting to at least one of the two plates 68 or 69. This sudden change of flow direction further facilitates recombination of the rest of any ozone particle in the airflow past the recombination unit 60.

A further optional unit shown in FIG. 2 is a screening unit 62b for the UV light that has elongated rounded openings shown in the enlarged picture of FIG. 2d, and the role of this screening unit 62b is to prevent passage of UV light out of the housing 10. The light will not be able to pass through these openings past the previous units.

The operation of the device according to the invention is as follows. The contaminated air that might contain bacteria and viruses enter the device through the holes of the front plate 11, and the fan 20 drives air in axial direction Z. The contaminated air enters the interior space of the mirror box 30. There when the germicidal UV C lamp 40 is driven by the supply unit 41 by the pulses of around 100 Volt and having a frequency around 16 KHz will light on and issues pulsating light rays in the UV-C range. These light pulses are lethal to bacteria and viruses. As known short-wave ultraviolet light disrupts DNA base pairing, causing formation of pyrimidine dimers, and leads to the inactivation of bacteria, viruses, and protozoa. The light will reach all parts of the interior of the mirror box 30 and the light-reflecting inner surface increases the intensity of the light in all parts of the interior. Because of the use of high frequency pulses the effects of the light on the viruses will be more intensive and a smaller light intensity will have the same destroying effect as what can be reached by a continuous light of much higher intensity.

In addition, when the six ozone generators 50a to 50f around the UV lamp 40 receive high frequency excitation, the pulsating electric field established under the effect of the above 40 kV voltage difference between opposite points of the outer and internal windings will generate corona discharge. Such discharges energize nitrogen oxide molecules, whereby nitrogen-monoxide and $O_3$ (ozone) are generated accompanied by the appearance of a special blue light. Ozone is an aggressive gas that destroys the DNS of the living cells present. Such cells have been previously at least weakened or killed under the effect of the UV-C light. With destroyed DNS the virus and bacteria cells will be unable to multiply and function.

The simultaneous presence of ozone and UV-C light has a synergistic effect in the sense that much less ozone and a smaller intensity of UV light will be needed for attaining the same destroying effect as otherwise it would be necessary if only UV-C light or only ozone was used. The use of pulses further strengthens this effect.

By the time the air flows through the interior of the mirror box, all bacteria and viruses present will become inactivated or totally killed, therefore the air flowing out of the mirror box 30 will be clean of viruses and other contaminating germs.

The appearance of blue light as a side effect of the generation of ozone provides assistance in adjusting the voltage, frequency and pulse duty cycle. On the mirror box 30 one can provide a small inspection hole for sensing such a blue light, or a light sensor can be arranged in the box, and the parameters of the PWM supply unit 41 can be adjusted by watching the appearance of the blue light and adjusting these parameters to the level when such light appears and stays through a longer period.

Although the amount of ozone required for triggering the virus killing effects is not too high, safety rules prevent the leading of even small volume of ozone in rooms where persons can be present. The ozone recombination unit 60 shown in FIG. 8 has the task to facilitate the recombination of ozone to normal two atom oxygen gas before leaving the device.

The direction of the momentary electric field in the direction Z is always opposite in the first gap between the adjacent first planes of the outer and inner windings 63, 64 and in the next gap between the adjacent second planes of the inner and outer windings 64, 63. As the gas molecules move in the direction Z, they are exposed to such a pulsating and changing electric field that causes an intensive movement of the molecules that facilitates the recombination of the instable ozone again to two atom normal $O_2$ molecules. This recombination effect depends on the voltage, frequency and duty cycle of the pulses coupled to the two windings 63, 64. Because the human smell is very sensitive to ozone, even the smallest concentration in the air leaving the device can be sensed. Therefore the parameters of the pulsated signal i.e. frequency, duty cycle and voltage can be finely adjusted so that in spite of substantial presence of ozone in the mirror box 30 ozone smell cannot be sensed in the out flowing air. As mentioned earlier, the best recombination data were obtained at a pulse voltage of 40 KV, and a frequency of around 16 kHz, and a duty cycle of around 70%.

The ozone recombination unit 60 can be realized in several different ways as shown in the preferred embodiment, because the recombination takes place under the effect of a pulsated voltage signal that generates sufficiently high field strength within the unit. The filter 62a further increases the efficiency of the recombination process, while the UV filter 62b prevents UV Light from leaving the device.

While the ozone recombination unit 60 performs an excellent function by recombining ozone generated in the mirror box 30, the recombination of ozone can be utilized in a number of different ways.

In summary, it can be said that the embodiment shown provides safe and efficient air disinfection with minimum amount of energy, as the synergistic effect of the simultaneous use of the UV C lamp 41 and the ozone generators around it require much less energy as if they were used as self standing air disinfection units.

While the suggested arrangement that six ozone generators surround the UV C lamp is preferred as it utilizes efficiently the available flow space, different arrangements and less number of ozone generators can also perform good disinfection effects. The same concerns the use of mirroring internal surfaces, without such design the operation can be also good, perhaps only the energy consumption would be higher.

The adjustment of the operation requires calibration, because the airflow rate, the excitation of the UV-C lamp, the amount of ozone generated and the adjustment of the ozone recombination unit should be coordinated, and this coordination should be based on proper calibration.

The device can be used in any direction i.e. with either horizontal or vertical airflow, and it is the task of disinfection and the nature of the room and the position of people in the room that define the optimum position of the device. It can be preferred if in larger spaces instead of using a single device with higher airflow rate, the use of a plurality of smaller devices distributed in the area can be more preferred.

The invention cannot be limited therefore to the preferred embodiments shown.

The invention claimed is:

1. Air disinfection device using ozone for killing bacteria and viruses with an ozone recombination unit, comprising a housing (10), a fan (20) arranged in the housing (10) for forcing air to pass through the housing, an ozone generator (50) included in the housing (10) and arranged in a separate box (30) which is positioned across a path of the airflow, said ozone generator (50) is electrically driven by a supply unit (41) connecting a voltage to said ozone generator (50) to excite corona discharge, wherein a germicidal lamp (40) emitting UV-C light is arranged in said box (30), both the germicidal lamp (40) and the ozone generator (50) are driven by electric pulses having a frequency over 10 KHz, and an ozone recombination unit (60) is arranged behind the box (30) across the airflow passage to neutralize ozone included in the air flow that comprises at least two windings (63, 64) each having at least one surface comprised of respective spaced wires positioned across the airflow path and connected to another supply unit (61) coupling a pulsated voltage with a repetition frequency over 10 KHz between the windings (63, 64), wherein said voltage is smaller than required for generating a corona discharge but sufficiently high to force ozone to get recombined into oxygen.

2. The device as claimed in claim 1, wherein the ozone generator (50) comprises a tube of an electrically insulating material and respective windings are arranged around the outside of the tube and within the interior of the tube, wherein the outer winding substantially covers the inner winding so that the distance between them is constituted by the thickness of the tube.

3. The device as claimed in claim 2, wherein the germicidal lamp (40) is arranged centrally in the box (30) and a predetermined number of identically designed ozone generators (50a, ..., 50f) are arranged around the lamp (40) in even angular distribution, wherein the windings of all of the ozone generators are connected in parallel.

4. The device as claimed in claim 3, wherein the number of the ozone generators (50) is six.

5. The device as claimed in claim 1, wherein the interior surface of the box (30) is at least partly light reflective.

6. The device as claimed in claim 1, wherein a width, frequency and amplitude of said pulses coupled to said germicidal lamp (40) to the ozone generators (50a to 50f) and to said ozone recombining unit (60) can be controlled within a predetermined range.

7. The device as claimed in claim 3, wherein the box (30) has a planar front plate (31) and a planar rear plate (32) and both of them comprise a central circular piece (33) in which an end portion of said lamp (40) is held, and a ring-shaped opening (34) is formed around the circular piece (33) in which ends of the tubes of the ozone generators (50a to 50f) are fixed.

8. The device as claimed in claim 1, wherein the ozone generators (50a to 50f) are driven by a voltage around 40 KV and a frequency around 40 kHz, and the windings (63, 64) of the ozone recombination unit (60) are driven by pulses around 40 KV and frequency around 16 KHz.

9. The device as claimed in claim 1, wherein the germicidal lamp is driven by pulses with an intensity of around 100 Volt and frequency of around 16 KHz.

10. The device as claimed in claim 1, wherein after the ozone recombining unit (60) an additional ozone filter (62a) is arranged across the flow path which comprises a pair of perforated plates (68, 69) with non-overlapping perforations along the direction of the flow path.

11. The device as claimed in claim 1, wherein a UV filter (62b) is arranged across the flow path just before an outflow side of the box (30) which comprises a perforated plate.

12. The device as claimed in claim 1, wherein in the ozone recombination unit (60) the windings (63, 64) are wound on respective first and second frames (65, 66), wherein the windings (63, 64) comprise linear spaced wires and the wires are wound to have respective wired planes both at the front and the rear surface of the associated frame (65, 66), and the second winding (64) is an inner winding (64) wound on the second or inner frame (66) and being arranged within the first or outer frame (65) of the first or outer winding (63), and the wires of the first and second windings extend normal to each other and to the direction of airflow.

13. The device as claimed in claim 1, wherein said fan (20) has an adjustable speed and a separate supply unit (21) is connected to it and supplying width modulated pulses having a frequency adjustable between 300 rpm and 1500 rpm for the adjustment of the speed thereof.

* * * * *